United States Patent
Suessenbach et al.

(10) Patent No.: US 9,773,342 B2
(45) Date of Patent: Sep. 26, 2017

(54) BARYCENTRIC FILTERING FOR MEASURED BIDERECTIONAL SCATTERING DISTRIBUTION FUNCTION

(71) Applicant: Nvidia Corporation, Santa Clara, CA (US)

(72) Inventors: Andreas Suessenbach, Wurselen (DE); Markus Tavenrath, Wurselen (DE)

(73) Assignee: Nvidia Corporation, Santa Clara, CA (US)

( * ) Notice: Subject to any disclaimer, the term of this patent is extended or adjusted under 35 U.S.C. 154(b) by 123 days.

(21) Appl. No.: 14/165,366

(22) Filed: Jan. 27, 2014

(65) Prior Publication Data

US 2015/0213641 A1 Jul. 30, 2015

(51) Int. Cl.
*G06T 15/80* (2011.01)
*G06T 15/50* (2011.01)
*G01N 21/47* (2006.01)
*G06T 13/20* (2011.01)

(52) U.S. Cl.
CPC ....... *G06T 15/506* (2013.01); *G01N 21/4738* (2013.01); *G06T 13/20* (2013.01)

(58) Field of Classification Search
None
See application file for complete search history.

(56) References Cited

U.S. PATENT DOCUMENTS

| | | | | |
|---|---|---|---|---|
| 7,830,522 B2* | 11/2010 | Han | ..................... | G01N 21/474 356/445 |
| 2005/0099418 A1* | 5/2005 | Cabral | ................... | G06T 15/04 345/419 |
| 2007/0165035 A1* | 7/2007 | Duluk, Jr. | ................ | G06T 1/60 345/506 |
| 2009/0167763 A1* | 7/2009 | Waechter | ................ | G06T 15/06 345/426 |
| 2011/0043812 A1* | 2/2011 | Han | ....................... | G01N 21/55 356/446 |
| 2011/0273450 A1* | 11/2011 | Baril | ........................ | G06T 15/04 345/426 |

OTHER PUBLICATIONS

Klosters ("http://www.apileofgrains.nl/vertex-interpolation-using-barycentric-coordinates-and-bilinear-filtering/" Vertex interpolation using Barycentric Coordinates and Bilinear Filtering, Oct. 2, 2012).*

(Continued)

*Primary Examiner* — Yu Chen

(57) ABSTRACT

The disclosure provides a method of determining reflected irradiance for a surface point on a surface whose reflectance properties are represented by a measured BSDF. Additionally, the disclosure provides a renderer and a computer program product. In one embodiment, the method includes: (1) determining u, v and w coordinates in the measured BSDF for the surface point based on an incoming and an outgoing ray direction, (2) selecting a triangle for barycentric interpolation based on values of the v and the w coordinates at the surface point and (3) performing the barycentric interpolation for evaluating the measured BSDF for the surface point.

15 Claims, 2 Drawing Sheets

(56) References Cited

OTHER PUBLICATIONS

Reza Nourai, "Barycentric Coordinates and Point in Triangle Tests", https://blogs.msdn.microsoft.com/rezanour/2011/08/07/barycentric-coordinates-and-point-in-triangle-tests/, Aug. 7, 2011.*

Wikipedia; Bidirectional Scattering Distribution Function; http://en.wikipedia.org/wiki/Bidirectional_scattering_distribution_function; Jan. 27, 2014; 3 pages.

Wikipedia; Barycentric Coordinate System; http://en.wikipedia.org/wiki/Barycentric_coordinate_system; Jan. 27, 2014; 6 pages.

* cited by examiner

BARYCENTRIC FILTERING FOR MEASURED BIDERECTIONAL SCATTERING DISTRIBUTION FUNCTION

TECHNICAL FIELD

This application is directed, in general, to rendering and, more specifically, to representing the scattering of light in a two-dimensional (2D) representation of a three-dimensional (3D) scene.

BACKGROUND

Creating life-like computer images, such as for video games, continues to be a challenge accepted by game designers and manufacturers of graphics processing systems. A graphics pipeline is typically used to create 2D images for video displays of 3D scenes. A graphics pipeline includes a sequence of steps or processes that turn a 3D model into a 2D raster representation for a display. Rendering is the process of extracting data from world space and rendering it into a screen space. World space is three-dimensional space that is often generated from a 3D model provided by a program run on a CPU. A graphics processing unit (GPU) receives instructions from the CPU program, generates the three-dimensional world space based thereon and renders a two-dimensional view for a display (i.e., screen space) from the world space. For example, the CPU program can be a video game that sends instructions to the GPU for rendering a two-dimensional view onto a display. A GPU uses a graphics pipeline for the rendering process that includes multiple processes such as shading and reflection/scattering that are used to describe the appearance of a surface in a scene.

Shading addresses the variation of material properties across the surfaces of a scene. Reflection and transmission deal with the relationship between light, incoming and outgoing, at a given point on a surface. Descriptions of the light relationship can be given in terms of a bidirectional scattering distribution function (BSDF). A description of BSDF can be found at http://en.wikipedia.org/wiki/Bidirectional_scattering_distribution_function. In short BSDF is a function having two parameters, an input and an output direction, that provides an output which is the reflected (transmitted) light based on the input parameters.

A measured BSDF stores measured scattering parameters as a 3D texture using the 3D coordinates of u, v and w for storing $\Phi_o$ (phi), $\theta_i$ (theta in) and $\theta_o$ (theta out), respectively. Measurements are by definition discrete. FIG. 1 illustrates the parameters of the measured BSDF function. The measured BSDF, having input parameters ($\Phi_o$, $\theta_i$, $\theta_o$) with $\theta_i$ in n1 steps in $(0, \pi n/2)$, $\theta_o$ in n2 steps in $(0, \pi/2)$ and $\Phi_o$ in n3 steps in $(0, \pi)$, maps incoming irradiance from $\theta_i$ to outgoing irradiance $\theta_o$ with $\Phi_o$ being the angle between the projections of those two rays onto the tangential plane. FIG. 1 illustrates the incoming (incident) light ray 110, the outgoing (scattered) light ray 120, the projections 112, 122, respectively, of the incoming and outgoing rays on the tangential plane, a sample point of a surface 130 of the tangential plane and the angle 140 between the projections of those rays 112, 122.

SUMMARY

In one aspect, the disclosure provides a method of determining reflected irradiance for a surface point on a surface whose reflectance properties are represented by a measured BSDF. In one embodiment, the method includes: (1) determining u, v and w coordinates in the measured BSDF for the surface point based on an incoming and an outgoing ray direction, (2) selecting a triangle for barycentric interpolation based on values of the v and the w coordinates at the surface point and (3) performing the barycentric interpolation for evaluating the measured BSDF for the surface point.

In another aspect, a renderer of a graphics processing system is disclosed. In one embodiment, the renderer includes: (1) a request interface configured to receive a request for a reflected irradiance of a surface point on a surface whose reflectance properties are represented by a measured BSDF and (2) a scattering determiner configured to employ barycentric interpolation to evaluate the measured BSDF for the surface point and provide the reflected irradiance.

In yet another aspect, the disclosure provides a computer program product having a series of operating instructions stored on a non-transitory computer readable medium that direct the operation of a processor when initiated to perform a method of determining reflected irradiance for a surface point on a surface whose reflectance properties are represented by a measured BSDF. In one embodiment, the method of the computer program product includes: (1) determining u, v and w coordinates in the measured BSDF for the surface point based on an incoming and an outgoing ray direction, (2) comparing a value of the v coordinate to a value of the w coordinate at the surface point, (3) selecting a triangle for barycentric interpolation based on the comparing, wherein the surface point is located within the triangle and (4) performing the barycentric interpolation for evaluating the measured BSDF for the surface point.

BRIEF DESCRIPTION

Reference is now made to the following descriptions taken in conjunction with the accompanying drawings, in which.

DETAILED DESCRIPTION

A measured BSDF is a discrete data set storing the reflectance properties of a material. Accordingly, measured BSDFs do not include scattering samples for non-discrete angles but instead store samples for discrete angles, e.g., one degree, two degrees, three degrees, etc. Since samples are not provided for each scattering, filtering of the measured BSDF data is performed to render an image. As such, a renderer interpolates the measured BSDF samples to obtain the reflectance properties for surface points with angles ($\Phi_o$, $\theta_i$, $\theta_o$), which are not sample points of the measured BSDF. Typically, a renderer determines the texture space values for a surface point using linear interpolation to determine each of the 3D samples.

It is realized herein that measured BSDF of a material, such as a specular material, has large values along a diagonal and very small values off of the diagonal. The measured BSDF parameters, therefore, form a ridge along a diagonal. Standard linear interpolation, however, generates ripples when interpolating along the diagonal of the specular material when displayed. A diagonal as used herein is a two dimensional slide of two coordinates for a fixed third coordinate. For example, the 2D slide of vw for a fixed u.

It is further realized herein that the rendering results of an image are improved by employing barycentric filtering for interpolating along the diagonals in the vw-slide for the measured BSDF. Accordingly, the disclosure provides a method of determining reflected irradiance for a surface point employing barycentric filtering for the interpolation instead of bi-linear interpolation.

Figure 1:
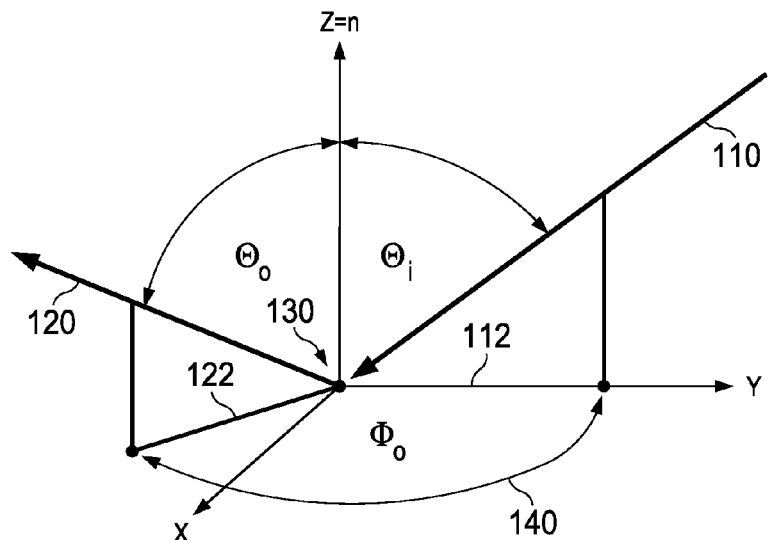
FIG. 1 illustrates the parameters of a measured BSDF.
Figure 2:
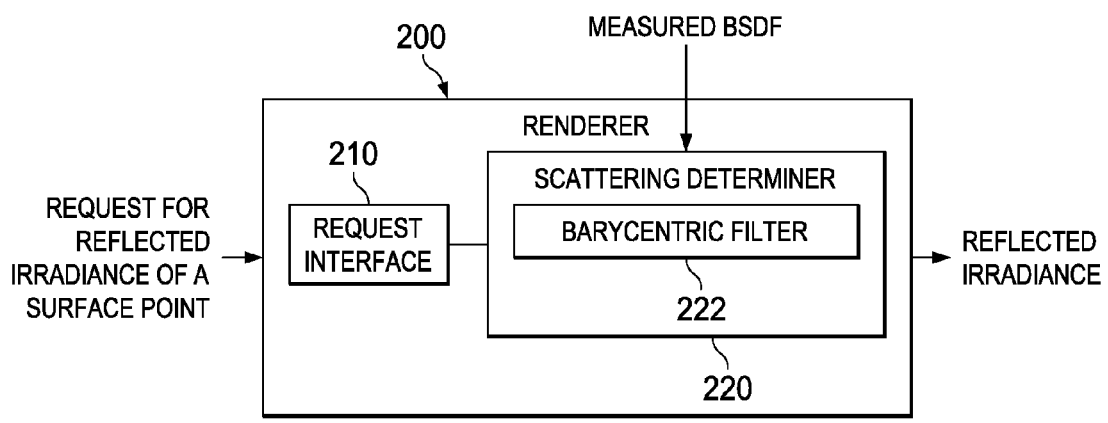
FIG. 2 illustrates a block diagram of an embodiment of a renderer constructed according to the principles of the disclosure.

FIG. 2 illustrates a high-level block diagram of an embodiment of a renderer 200 constructed according to the principles of the disclosure. In one embodiment, the renderer 200 is included within a GPU. The renderer 200 may be part of a graphics pipeline of a graphics processing system implemented by a CPU and a GPU or a combination thereof. In one embodiment, the graphics processing system includes an application stage, a world space and a screen space, wherein the application stage is configured to provide a 3D model to the world space and the world space is configured to receive the 3D model and generate 3D geometry data for the screen space. The graphics pipeline or system can include programmable stages and/or fixed function stages that have circuitry configured to perform a dedicated function. A programmable processing stage includes the necessary processors and memory to perform dedicated functions of a pipeline stage. In one embodiment, the processors can be specifically configured for processing highly parallel code. In other embodiments, general processing units with scalar cores can be implemented as programmable stages.

The renderer 200 is configured to employ information from the measured BSDF to obtain the reflected irradiance for surface points. The renderer 200 can provide the reflected irradiance to a shader of the graphics processing pipeline for pixel shading. In contrast to a conventional renderer, the renderer 200 employs barycentric interpolation to determine the reflected irradiance for surface points. The renderer 200 includes a request interface 210 and a scattering determiner 220 having a barycentric filter 222 for the barycentric interpolation.

The request interface 210 is configured to receive a request for reflected irradiance of a surface point. The surface point is a point on a surface to be rendered for a 2D view, wherein the reflectance properties of the surface are specified by a measured BSDF. The request can be received from a shader of a graphics processing pipeline for providing a 2D view for, for example, a video game.

The scattering determiner 220 is configured to provide reflected irradiance for the renderer 200 including providing the reflected irradiance for surface points. In contrast to a conventional renderer employed with measured BSDF, the scattering determiner 220 does not perform linear interpolation to determine each BSDF value for the surface point. For example, the scattering determiner 220 does not perform linear interpolation to determine an interpolated value for the v and w coordinates of the surface point. Instead, the scattering determiner 220 employs the barycentric interpolator 222 to perform barycentric interpolation.

As mentioned above, in one embodiment the barycentric filter 222 is configured to employ barycentric interpolation to determine an interpolated value for the v and w coordinates for the surface point. The scattering determiner 220 is configured to employ linear interpolation to determine the sample for the u coordinate for the surface point according to conventional means. The scattering determiner 220 can then employ the interpolated sample for the u, v and w coordinates for evaluating the measured BSDF for the surface point.

The barycentric filter 222 is configured to determine the interpolated value for the v and w coordinates for surface points employing sample points of the measured BSDF. In one embodiment, the barycentric filter 222 selects a triangle for performing barycentric interpolation wherein the vertices of the triangle are sample points of the measured BSDF. The values of the measured BSDF for each of the sample point vertices are the values that are used for the barycentric interpolation.

Figure 3:
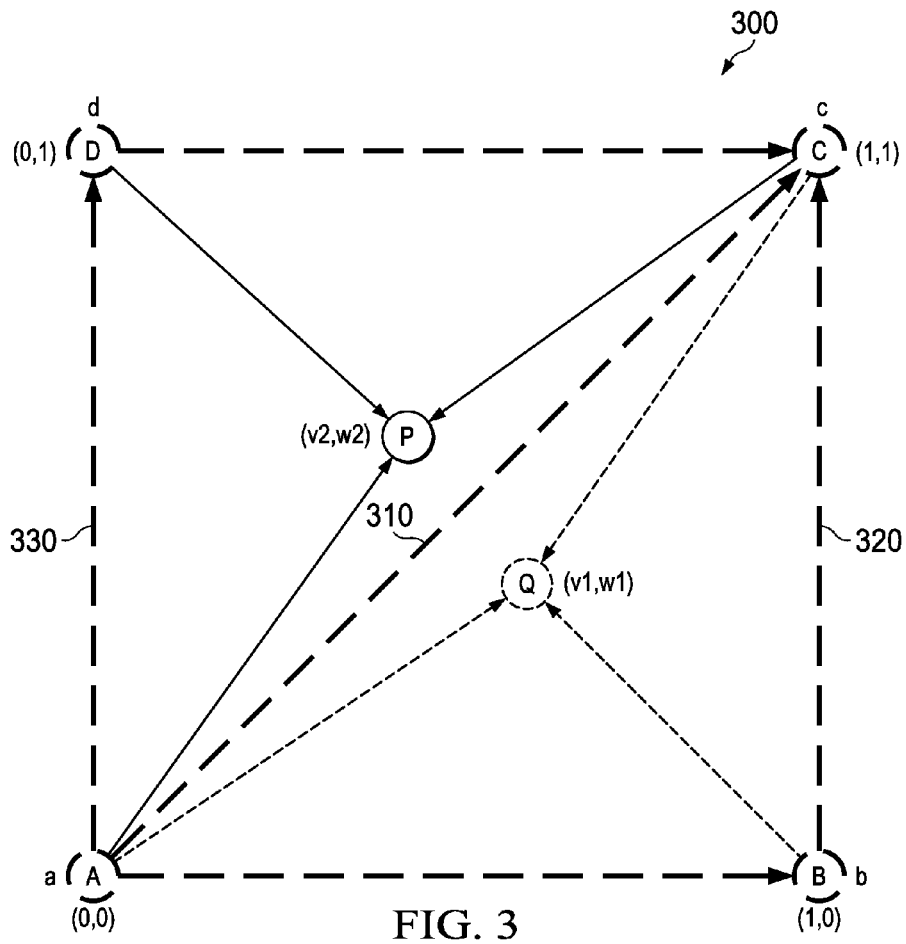
FIG. 3 illustrates four adjacent sample points (a, b, c, d) of a measured BSDF and the barycentric filtering of two arbitrary surface points (p, q)

In one embodiment, the barycentric filter 222 is configured to determine the interpolated value for the v-w coordinates of a surface point according to the example provided by FIG. 3. FIG. 3 illustrates four adjacent sample points (a, b, c, d) of a measured BSDF and the barycentric filtering of two arbitrary surface points (p, q). The four adjacent sample points are located on a 2D plane 300.

The surface points p and q are proximate a diagonal 310 between sample points a and c. Employing bilinear interpolation to determine the reflected irradiance of the surface points p and q as in conventional renderers would result in ripples along the reflection. Instead, the barycentric filter 222 employs a triangle defined by three of the sample points a, b, c and d, to calculate the barycentric coordinates for the surface point. Two triangles are identified in FIG. 3 as triangle 320 and triangle 330. Information about a barycentric coordinate system can be found at http://en.wikipedia.org/wiki/Barycentric_coordinate_system, and is incorporated herein by reference.

In FIG. 3, arrows from each of the designated coordinates a, b, c and d are used to indicate the designated points that are used to calculate the barycentric coordinates for each of the surface points p and q. Selection of either triangle 320 or triangle 330 is based on a comparison between the v and w coordinates of the surface points. Consider first the sample point q. For surface point q, the value of v1 is greater than the value of w1 wherein the values of v1 and w1 are between zero and one. As such, the triangle 320 is selected for barycentric interpolation of surface point q. The barycentric filter 222: (1) chooses the relative texels for sample point q as ta(0,0), tb(1,0) and tc(1,1), (2) computes the barycentric coordinates for sample point q employing Equation 1 below and (3) employs the calculated barycentric coordinates for the texels of the surface point q.

$$u = 1 - q(v)$$

$$v = q(v) - q(w)$$

$$w = q(w) \hspace{4em} \text{Equation 1}$$

In Equation 1, q(v) is the v coordinate of sample point q on the 2D plane 300 and q(w) is the w coordinate of sample point q on the 2D plane 300. As illustrated in FIG. 3, these are v1 and w1, respectively.

If sample point p, the barycentric filter 222 determines that the v coordinate v2 of sample point p is less than the w coordinate w2 of sample point p. As such the triangle 330, defined by sample points a, c and d, is used to calculate the barycentric coordinates of sample point p employing the process described above with respect to surface point q.

Thus, in one embodiment, the barycentric filter 222 can select triangle 320 as defined by a-c-b or triangle 330 as defined by a-c-d depending on the position of the surface point, either q or p, relative to the diagonal 310. The barycentric filter 222 can then calculate the barycentric coordinates (u,v,w) of the sample point p or q in the respective triangle. The resulting interpolated value would then be used to determine the reflected irradiance of the surface point. With this interpolation method, sample points at and close to the diagonal 310 get lower weights from the off-diagonal points b and d. As such, features along the diagonal 310 are preserved in the 2D view.

Figure 4:
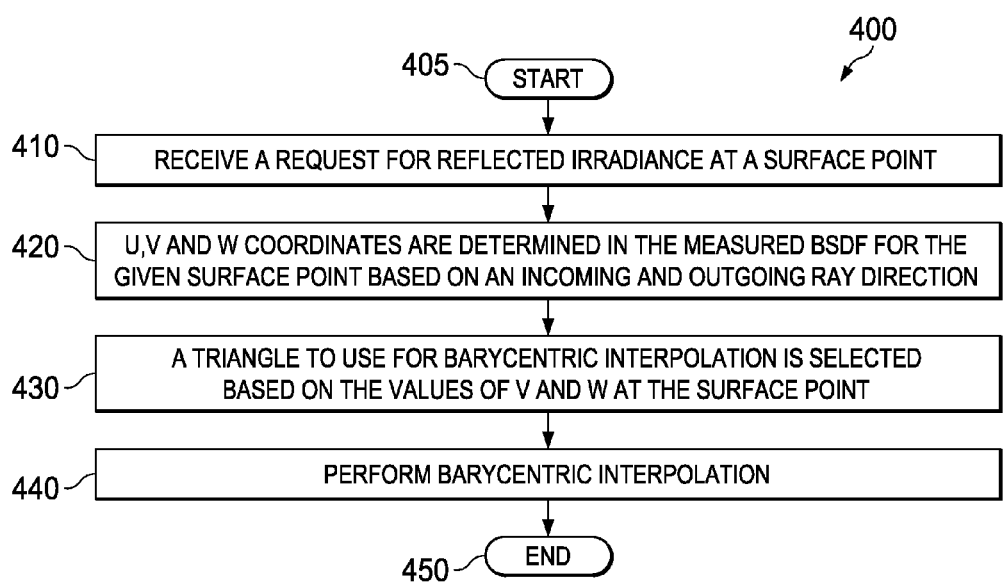
FIG. 4 illustrates a flow diagram of an embodiment of a method of determining the reflected irradiance for a surface point carried out according to the disclosure.

FIG. 4 illustrates a flow diagram of an embodiment of a method 400 of determining the reflected irradiance for a surface point carried out according to the disclosure. The surface point may be proximate a diagonal between two known sample points of a measured BSDF. The method may be carried out by a GPU, a renderer of a GPU or another component of a graphics pipeline or processing system. In one embodiment, the method or at least part of the method is implemented as a computer program product. The method begins in a step 405.

In a step 410, a request is received for the reflected irradiance of a point on a surface whose reflectance properties are specified by a measured BSDF. The surface point might not be a sample point of the measured BSDF for the material.

In a step 420, u,v,w coordinates are determined in the measured BSDF for the given surface point based on an incoming and outgoing ray direction. Accordingly, a $\theta_i$ and a $\theta_o$ from the measured BSDF are employed to determine the nearest sample points of the measured BSDF for the surface point. In some embodiments, four sample points are determined from the incoming and outgoing ray direction, wherein the four sample points are the nearest sample points surrounding the surface point In a step 430, the triangle to use for barycentric interpolation is determined depending on the v, w values at the sample point. Regarding FIG. 3 as an example, if the value of the v coordinate is greater than the value of the w coordinate (i.e., point q), then the triangle 320 is selected and the following relative texels are chosen for the barycentric interpolation: ta(0,0), tb(1,0) and tc(1,1). If the value of the v coordinate is less than the value of the w coordinate (i.e., point p), then the triangle 330 is selected and the following relative texels are chosen for the barycentric interpolation: ta(0,0), tb(0,1) and tc(1,1).

Barycentric interpolation is performed in a step 440 to evaluate the measured BSDF for the given set of parameters. The selected triangle from step 430 is used for the barycentric interpolation to provide the desired interpolation for v and w, i.e., the v-w plane for the surface point. The interpolated value can then be employed to determine the reflected irradiance of the surface point. The method 400 ends in a step 450.

While the method disclosed herein has been described and shown with reference to particular steps performed in a particular order, it will be understood that these steps may be combined, subdivided, or reordered to form an equivalent method without departing from the teachings of the present disclosure. Accordingly, unless specifically indicated herein, the order or the grouping of the steps is not a limitation of the present disclosure.

The above-described methods may be embodied in or performed by various conventional digital data processors, microprocessors or computing devices, wherein these devices are programmed or store executable programs of sequences of software instructions to perform one or more of the steps of the methods, e.g., steps of the method of FIG. 4. The software instructions of such programs may be encoded in machine-executable form on conventional digital data storage media that is non-transitory, e.g., magnetic or optical disks, random-access memory (RAM), magnetic hard disks, flash memories, and/or read-only memory (ROM), to enable various types of digital data processors or computing devices to perform one, multiple or all of the steps of one or more of the above-described methods, e.g., one or more of the steps of the method of FIG. 4. Additionally, an apparatus may be designed to include the necessary circuitry or programming to perform each step of a method disclosed herein.

Portions of disclosed embodiments may relate to computer storage products with a non-transitory computer-readable medium that have program code thereon for performing various computer-implemented operations that embody a part of an apparatus, system or carry out the steps of a method set forth herein. Non-transitory used herein refers to all computer-readable media except for transitory, propagating signals. Examples of non-transitory computer-readable media include, but are not limited to: magnetic media such as hard disks, floppy disks, and magnetic tape; optical media such as CD-ROM disks; magneto-optical media such as floptical disks; and hardware devices that are specially configured to store and execute program code, such as ROM and RAM devices. Examples of program code include both machine code, such as produced by a compiler, and files containing higher level code that may be executed by the computer using an interpreter.

Those skilled in the art to which this application relates will appreciate that other and further additions, deletions, substitutions and modifications may be made to the described embodiments.

What is claimed is:

1. A method of determining reflected irradiance for a surface point on a surface whose reflectance properties are represented by a measured Bidirectional scattering distribution function (BSDF), comprising:
   determining u, v and w coordinates in said measured BSDF for said surface point based on an incoming and an outgoing ray direction;
   selecting a triangle, defined by sample points of said measured BSDF that are adjacent said surface point, for barycentric interpolation based on a comparison of values of said v and said w coordinates at said surface point; and
   evaluating said measured BSDF for said surface point by performing said barycentric interpolation that provides a sample interpolated value for said v and w coordinates of said surface point and a linear interpolation that determines a sample interpolated value for said u coordinate of said surface point, wherein said determining, selecting and evaluating are carried out using a renderer of a graphics processing system.

2. The method as recited in claim 1 wherein vertices of said triangle are sample points of said measured BSDF.

3. The method as recited in claim 2 wherein values of said measured BSDF for each of said vertices are used for said barycentric interpolation.

4. The method as recited in claim 1 wherein evaluating said measured BSDF for said surface point includes employing said sample interpolated values for said u, v and w coordinates.

5. The method as recited in claim 1 wherein said measured BSDF is for a specular material.

6. A renderer of a graphics processing system, comprising:
   a request interface configured to receive a request for a reflected irradiance of a surface point on a surface whose reflectance properties are represented by a measured Bidirectional scattering distribution function (BSDF); and a scattering determiner configured to employ barycentric interpolation by selecting a triangle defined by sample points of said measured BSDF that are adjacent said surface point based on a comparison of values of v and w coordinates of said surface point to evaluate said measured BSDF for said surface point and provide said reflected irradiance, wherein said barycentric interpolation provides a sample interpolated value for said v and w coordinates of said surface point, and said scattering determiner is further configured to perform a linear interpolation to provide a sample interpolated value for a third coordinate of said surface point.

7. The renderer as recited in claim 6 wherein said scattering determiner includes a barycentric filter configured to perform said barycentric interpolation.

8. The renderer as recited in claim 7 wherein said scattering determiner determines said adjacent sample points from an incoming and outgoing ray direction of said measured BSDF.

9. The renderer as recited in claim 7 wherein said scattering determiner is configured to evaluate said measured BSDF for said surface point employing said sample interpolated values for said three dimensional coordinates.

10. The renderer as recited in claim 6 wherein said surface point is not a sample point of said measured BSDF.

11. A computer program product having a series of operating instructions stored on a non-transitory computer readable medium that direct the operation of a processor when initiated to perform a method of determining reflected irradiance for a surface point on a surface whose reflectance properties are represented by a measured Bidirectional scattering distribution function (BSDF), said method comprising:

determining u, v and w coordinates in said measured BSDF for said surface point based on an incoming and an outgoing ray direction;

comparing a value of said v coordinate to a value of said w coordinate at said surface point;

selecting a triangle, defined by sample points of said measured BSDF that are adjacent said surface point, for barycentric interpolation based on said comparing, wherein said surface point is located within said triangle; and evaluating said measured BSDF for said surface point by performing said barycentric interpolation that provides a sample interpolated value for said v and w coordinates of said surface point and a linear interpolation that provides a sample interpolated value for said u coordinate of said surface point.

12. The computer program product as recited in claim 11 wherein vertices of said triangle are sample points of said measured BSDF.

13. The computer program product as recited in claim 12 wherein values of said measured BSDF for each of said vertices are used for said barycentric interpolation.

14. The computer program product as recited in claim 11 wherein evaluating said measured BSDF for said surface point includes employing said sample interpolated values for said u, v and w coordinates.

15. A graphics processing unit having stored thereon the computer program product of claim 11.

* * * * *